United States Patent
Katsuno et al.

(10) Patent No.: US 8,951,976 B2
(45) Date of Patent: Feb. 10, 2015

(54) PROGRESSION INHIBITOR FOR DISEASE ATTRIBUTED TO ABNORMAL ACCUMULATION OF LIVER FAT

(75) Inventors: Kenji Katsuno, Nagano (JP); Yoshikazu Fujimori, Nagano (JP); Masayuki Isaji, Nagano (JP)

(73) Assignee: Kissei Pharmaceutical Co., Ltd., Nagano (JP)

( * ) Notice: Subject to any disclaimer, the term of this patent is extended or adjusted under 35 U.S.C. 154(b) by 791 days.

(21) Appl. No.: 12/511,654

(22) Filed: Jul. 29, 2009

(65) Prior Publication Data
US 2009/0286751 A1 Nov. 19, 2009

Related U.S. Application Data

(63) Continuation of application No. 11/572,251, filed as application No. PCT/JP2005/013262 on Jul. 19, 2005, now abandoned.

(30) Foreign Application Priority Data

Jul. 21, 2004 (JP) ................................ 2004-213675

(51) Int. Cl.
| | | |
|---|---|---|
| A61K 31/70 | (2006.01) | |
| A61K 31/7028 | (2006.01) | |
| A61K 31/155 | (2006.01) | |
| A61K 31/4427 | (2006.01) | |
| A61K 31/57 | (2006.01) | |
| A61K 31/7036 | (2006.01) | |

(52) U.S. Cl.
CPC ........... *A61K 31/7028* (2013.01); *A61K 31/155* (2013.01); *A61K 31/4427* (2013.01); *A61K 31/57* (2013.01); *A61K 31/7036* (2013.01)
USPC .......................................................... 514/25

(58) Field of Classification Search
None
See application file for complete search history.

(56) References Cited

U.S. PATENT DOCUMENTS

| | | | |
|---|---|---|---|
| 6,872,706 B2 | 3/2005 | Fujikura et al. | |
| 6,972,283 B2 * | 12/2005 | Fujikura et al. | 514/27 |
| 7,045,665 B2 * | 5/2006 | Fujikura et al. | 568/744 |
| 7,375,090 B2 | 5/2008 | Himmelsbach et al. | |
| 2003/0045553 A1 * | 3/2003 | Bussolari et al. | 514/340 |
| 2004/0138148 A1 | 7/2004 | Fushimi et al. | |
| 2004/0147729 A1 | 7/2004 | Fujikura et al. | |

FOREIGN PATENT DOCUMENTS

| | | |
|---|---|---|
| EP | 1 367 060 A1 | 12/2003 |
| WO | 01/27128 A1 | 4/2001 |
| WO | 01/68660 A1 | 9/2001 |
| WO | 02/28872 A1 | 4/2002 |
| WO | 02/064606 A1 | 8/2002 |
| WO | 02/080936 A1 | 10/2002 |

OTHER PUBLICATIONS

English Translation of Toshifumi, Azuma, "Nash no Chiryo", Igaku no Ayumi, 2003, vol. 206, No. 5, pp. 347-352.
Toshifumi, Azuma, "Nash no Chiryo", Igaku no Ayumi, 2003, vol. 206, No. 5, pp. 347 to 352; full text; particularly, pp. 350-351, in Japanese.
Nawano, M. et al.; Hyperglycemia contributes insulin resistence in hepatic and adipose tissue but not skeletal muscle of ZDF rates, Am. J. Physiol. Endocrinol. Metab, 2000, vol. 278, No. 3, p. E535-43, full text; particularly, p. E535, Abstract.
Lazaridis, K. N. et al., Kinetic and molecular identification of sodium-dependent glucose transporter in normal rat cholangiocytes, Am. J. Physiol., 1997, vol. 272, No. 5, Pt., 1.; p. G1168-74.
Weekly Electronic Newspaper for Pharmacies No. 1341, Sep. 15, 2003, 1st paragraph in p. 1, 2nd Paragraph in p. 4.
Taiwanese Search Report for App. No. 094124672 dated May 27, 2011.

\* cited by examiner

*Primary Examiner* — Traviss C McIntosh, III
(74) *Attorney, Agent, or Firm* — Sughrue Mion, PLLC

(57) ABSTRACT

The present invention provides pharmaceutical compositions useful as agents for the inhibition of progression of diseases associated with abnormal accumulation of liver lipids. In particular, the pharmaceutical compositions of the present invention which comprise as an active ingredient a sodium/glucose co-transporter 2 inhibitor are highly suitable as an agent for the inhibition of progression of not only common fatty liver but also non-alcoholic fatty liver disease (NAFL), non-alcoholic steatohepatitis (NASH), hypernutritive fatty liver, diabetic fatty liver, alcoholic fatty liver disease toxic fatty liver or the like.

4 Claims, No Drawings

PROGRESSION INHIBITOR FOR DISEASE ATTRIBUTED TO ABNORMAL ACCUMULATION OF LIVER FAT

This is a Continuation Application of U.S. application Ser. No. 11/572,251 filed Jan. 17, 2007, which claims priority from JP 2004-213675 filed Jul. 21, 2004, the contents of which are incorporated herein by reference.

TECHNICAL FIELD

The present invention relates to an agent for the inhibition of progression of diseases associated with abnormal accumulation of liver lipids, which comprises as an active ingredient a sodium/glucose co-transporter 2 (hereinafter referred to as SGLT2).

BACKGROUND ART

The patients with disorders in which lipids are abnormally accumulated in liver, such as non-alcoholic steatohepatitis (NASH), hypernutritive fatty liver, diabetic fatty liver, alcoholic fatty liver, and toxic fatty liver as well as common fatty liver are increasing year by year. Above all, non-alcoholic steatohepatitis (NASH) is particularly acknowledged as a problem, because it exhibits serious symptoms (see non-Patent Reference 1 or 2). Moreover, it has been pointed out that abnormal lipid accumulation in liver causes liver inflammation or fibril formation in liver (liver cirrhosis) and makes shifts to serious disorders such as liver cancer (see non-Patent References 1 to 4), and thus, inhibiting this lipid accumulation is extremely important.

It is believed that various factors including recent lifestyle changes overlap each other and abnormalities in liver energy metabolism are caused and as a consequence, lipid accumulation in liver occurs. Therefore therapeutic modality is not uniform (see non-Patent Reference 5). Although presently, dietary therapy, exercise therapy, pharmacotherapy and the like are tried as remedies for lipid accumulation in liver, these modalities have difficulties in control or continuing implementation. Therefore, therapeutic effects are not always satisfied. Meanwhile, in pharmacotherapy, polyene-phosphatidyl choline preparation is only listed under coverage. As described above, satisfied treatment modality for lipid accumulation in liver has not been established, and thus development of more effective drug for lipid accumulation has been desired.

It is known that SGLT2 inhibitors are drugs which exhibit blood glucose-lowering action by inhibiting sugar reabsorption in kidney, and are useful as drugs for the prevention or treatment of diabetes mellitus (for example, see Patent References 1 to 19). In addition, as to SGLT2 inhibitor, it has been also proposed that concurrent use of T-1095 represented by formula:

[Chem. 1] (T-1095)

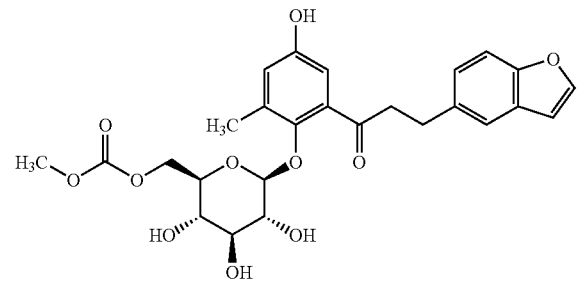

and a peroxisome proliferator-activated receptor (hereinafter referred to as PPAR) agonist or a retinoid X receptor (hereinafter referred to as RXR) agonist can suppress the onset of side effects such as fatty liver caused by PPAR agonists or RXR agonists, and therefore the dosage of PPAR agonist or RXR agonist can be reduced (see Patent Reference 20 or 21). However, it has not ever been known that SGLT2 inhibitors exhibit suppressive effects on abnormal accumulation of liver lipids as described in the present invention.

In the treatment of diabetic fatty liver, use of hypoglycemic agents has been studied (see non-Patent Reference 6). However, usefulness of diabetic drugs with blood glucose-lowering actions has been not confirmed, for example, it has been pointed out that tolbutamide does not exhibit suppressive effects on lipid accumulation in liver (see non-Patent Reference 7), and may adversely cause exacerbation of lipid accumulation in liver (see non-Patent Reference 6).

In addition, it has been reported that clofibrate of an antihyperlipidemic agent causes lipid accumulation in liver as a side effect, while it lowers neutral fat or cholesterol in blood (see Patent Reference 22). Furthermore, it has been reported that microsomal triglyceride transfer protein (hereinafter referred to as MTP) inhibitor of an antihyperlipidemic agent causes lipid accumulation in liver, while it lowers neutral fat or cholesterol in blood (see Patent References 23 and 24 and non-Patent References 8 and 9). As described above, in use of these antihyperlipidemic drugs, no correlation is observed in the amount of neutral fat or cholesterol between in blood and in liver, but induction of fatty liver is observed in some cases.

Patent Reference 1: International Publication WO02/28872 pamphlet;
Patent Reference 2: International Publication WO02/44192 pamphlet;
Patent Reference 3: International Publication WO02/53573 pamphlet;
Patent Reference 4: International Publication WO01/16147 pamphlet;
Patent Reference 5: International Publication WO01/68660 pamphlet;
Patent Reference 6: International Publication WO03/11880 pamphlet;
Patent Reference 7: International Publication WO03/00712 pamphlet;
Patent Reference 8: International Publication WO02/068440 pamphlet;
Patent Reference 9: International Publication WO02/68439 pamphlet;
Patent Reference 10: International Publication WO02/64606 pamphlet;
Patent Reference 11: International Publication WO03/80635 pamphlet;
Patent Reference 12: International Publication WO02/88157 pamphlet;
Patent Reference 13: International Publication WO02/36602 pamphlet;
Patent Reference 14: International Publication WO03/20737 pamphlet;
Patent Reference 15: International Publication WO01/74835 pamphlet;
Patent Reference 16: International Publication WO01/74834 pamphlet;
Patent Reference 17: Japanese Patent Publication 2003-012686;
Patent Reference 18: International Publication WO01/27128 pamphlet;
Patent Reference 19: International Publication WO03/99836 pamphlet;

Patent Reference 20: International Publication WO02/080936 pamphlet;

Patent Reference 21: International Publication WO02/080935 pamphlet;

Patent Reference 22: Japanese Patent Publication H8-119860;

Patent Reference 23: Japanese Patent Publication 2002-220345;

Patent Reference 24: International Publication WO03/075232 pamphlet;

Non-patent Reference 1: Hiromasa Ishii, IGAKU NOAYUMI (Journal of Clinical and Experimental Medicine), 2003, Vol. 206, No. 5, pp. 323-325;

Non-patent Reference 2: Naoki Tanaka and one person, KANZO (Acta Hepatologica Japonica), 2002, Vol. 43, No. 12, pp. 539-549;

Non-patent Reference 3: Kazuhiko Koike, IGAKU NOAYUMI (Journal of Clinical and Experimental Medicine), Vol. 206, No. 5, pp. 385-388;

Non-patent Reference 4: Koutaro Uchimura and three persons, RINSHO TO KENKYU (The Japanese Journal of Clinical and Experimental Medicine), 2003, Vol. 80, No. 3, pp. 503-506;

Non-patent Reference 5: Kenichiro Iwamura, KANZO (Acta Hepatologica Japonica), 1971, Vol. 12, No. 12, pp. 659-669;

Non-patent Reference 6: Kenichiro Iwamura, SAISIN-IG-AKU (The Medical Frontline), 1978, Vol. 33, No. 3, pp. 524-531;

Non-Patent Reference 7: A. Beringer and three persons, Deutsche Medizinische Wochenschrift, 1967, vol. 92, No., pp. 2388-2392;

Non-patent Reference 8: Ken Ohashi, Annual review. NAI-BUNPI, TAISHA 2000 (Internal Secretion, Metabolism 2000), Chugaiigaku Co. publication, pp. 17-23;

Non-Patent Reference 9: Junichi Osuga, NAIKA (Internal Medicine), 2002, vol. 89, No. 5, pp. 875-881.

DISCLOSURE OF THE INVENTION

Problem to be solved by the Invention

The object of the present invention is to provide useful pharmaceutical compositions for the inhibition of progression of the diseases associated with abnormal accumulation of liver lipids.

Means of Solving the Problems

In view of the above object, the present inventors have studied earnestly to find a compound having an effect to inhibit lipid accumulation in liver, and they acquired the surprising knowledge that SGLT2 inhibitor had an excellent effect inhibiting lipid accumulation, thereby forming the bases of the present invention.

That is, the present invention relates to:

[1] a pharmaceutical composition for the inhibition of progression of a disease associated with abnormal accumulation of liver lipids, which comprises as an active ingredient a SGLT2 inhibitor;

[2] a pharmaceutical composition as described in the above [1] wherein the SGLT2 inhibitor is 2-(4-methoxybenzyl)-phenyl β-D-glucopyranoside or a pharmaceutically acceptable salt thereof, or a prodrug thereof;

[3] a pharmaceutical composition as described in the above [1] or [2] which is used in combination with one or more selected from a group consisting of metformin, troglitazone, pioglitazone hydrochloride, bezafibrate and voglibose; and the like.

The term "SGLT2 inhibitor" as an active ingredient of the present invention means a compound inhibiting sugar reabsorption in kidney by inhibiting SGLT2 activity. As the SGLT2 inhibitor of the present invention, SGLT2 inhibitors described in the above Patent References 1 to 19 can be illustrated, and concrete examples of desirable execution mode include compounds selected from the following group and pharmaceutically acceptable salts thereof.

2-(4-Methoxybenzyl)phenyl β-D-glucopyranoside, 2-(4-methylbenzyl)phenyl β-D-glucopyranoside, 2-(4-ethylbenzyl)phenyl-D-glucopyranoside, 2-(4-isobutylbenzyl)-phenylβ-D-glucopyranoside, 2-(4-ethoxybenzyl)phenyl β-D-glucopyranoside, 2-(4-isopropoxybenzyl)phenyl β-D-glucopyranoside, 5-hydroxymethyl-2-(4-propoxybenzyl)-phenyl β-D-glucopyranoside, 2-(4-ethylbenzyl)-5-hydroxymethylphenyl β-D-glucopyranoside, 2-[4-(2-hydroxyethyl)-benzyl]-5-hydroxymethylphenyl β-D-glucopyranoside, 2-[4-(2-hydroxyethyl)benzyl]phenyl β-D-glucopyranoside, 2-[4-(3-hydroxypropyl)benzyl]phenyl β-D-glucopyranoside, 2-(4-ethylthiobenzyl)phenyl β-D-glucopyranoside, 2-(4-methoxybenzyl)phenyl 6-O-ethoxycarbonyl-β-D-glucopyranoside, 2-(4-methoxybenzyl)phenyl 6-O-methoxycarbonyl-β-D-glucopyranoside, 2-(4-methoxybenzyl)phenyl-6-O-[2-(methoxy)ethyloxycarbonyl]-β-D-glucopyranoside, 2-(4-methoxybenzyl)phenyl 6-O-hexanoyl-β-D-glucopyranoside, 2-(4-methoxybenzyl)phenyl 6-O-propionyl-β-D-glucopyranoside, 2-(4-methoxybenzyl)phenyl 6-O-butyryl-β-D-glucopyranoside, 2-(4-methoxybenzyl)phenyl 6-O-acetyl-β-D-glucopyranoside, 2-(4-methoxybenzyl)phenyl 6-O-isobutyryl β-D-glucopyranoside, 2-(4-methoxybenzyl)phenyl 6-O-ethylsuccinyl-β-D-glucopyranoside, 2-(4-methoxybenzyl)phenyl 6-O-isopropyloxy-carbonyl-β-D-glucopyranoside, 2-(4-methylbenzyl)phenyl-6-O-ethoxycarbonyl-β-D-glucopyranoside, 2-(4-methylbenzyl)-phenyl 6-O-methoxycarbonyl-β-D-glucopyranoside, 2-(4-ethylbenzyl)phenyl 6-O-ethoxycarbonyl-β-D-glucopyranoside, 2-(4-ethylbenzyl)phenyl 6-O-methoxycarbonyl-β-D-glucopyranoside, 5-amino-2-(4-ethylbenzyl)phenyl β-D-glucopyranoside, 2-[4-(3-hydroxypropyl)benzyl]-3,5-dimethyl-phenylβ-D-glucopyranoside, 2-[4-(2-hydroxyethyl)benzyl]-3,5-dimethylphenyl β-D-glucopyranoside, 2-(4-methoxybenzyl)-3,5-dimethylphenylβ-D-glucopyranoside, 2-(4-ethylbenzyl)-5-hydroxymethylphenyl 6-O-ethoxycarbonyl-β-D-glucopyranoside, 2-(4-ethylbenzyl)-5-pivaloyloxymethylphenyl β-D-glucopyranoside, 2-(4-ethylbenzyl)-5-hydroxymethylphenyl-6-O-butyryl-β-D-glucopyranoside, 5-acetoxy-2-(4-ethylbenzyl)phenyl 6-O-acetyl-β-D-glucopyranoside, 2-(4-ethylbenzyl)-5-(ethoxycarbonyloxymethyl)phenyl β-D-glucopyranoside, 2-(4-ethylbenzyl)-5-hydroxymethylphenyl 6-O-hexanoyl-β-D-glucopyranoside, 2-(4-ethylbenzyl)-5-hydroxymethylphenyl 6-O-pivaloyl-β-D-glucopyranoside, 2-(4-ethylbenzyl)-5-hydroxymethylphenyl-O-isobutyloxycarbonyl-β-D-glucopyranoside, 2-(4-ethylbenzyl)-5-hydroxymethylphenyl-O-isopropyloxycarbonyl-β-D-glucopyranoside, 2-[4-(2-benzyloxyethyl)benzyl]phenyl 6-O-ethoxycarbonyl-β-D-glucopyranoside, 2-[4-(2-benzyloxyethyl)benzyl]phenyl 6-O-acetyl-β-D-glucopyranoside, 2-[4-(2-acetoxyethyl)benzyl]phenyl 6-O-acetyl-β-D-glucopyranoside, 2-(4-pyrazole-1-ylbenzyl)-phenyl β-D-glucopyranoside, 2-[4-(4-hydroxypiperidin-1-yl)-benzyl]β-D-glucopyranoside, 3-(β-D-glucopyranosyloxy)-4-[(4-isopropoxyphenyl)methyl]-5-methyl-1H-pyrazole, 3-(β-D-glucopyranosyloxy)-5-methyl- 4-[(4-propylphenyl)methyl]-1H-pyrazole, 3-(β-D-glucopyranosyloxy)-4-[(4-isobutylphenyl)-methyl]-5-methyl-1H-pyrazole, 3-(β-D-glucopyranosyloxy)-5-methyl-4-[(4-propoxyphenyl)methyl]-1H-pyrazole, 4-[(4-ethoxyphenyl)methyl]-3-(β-D-glucopyranosyloxy)-5-methyl-1H-pyrazole, 3-(β-D-glucopyranosyloxy)-5-methyl-4-[(4-methylthiophenyl)methyl]-1H-pyrazole, 5-ethyl-3-(β-D-glucopyranosyloxy)-4-[(4-methylthiophenyl)methyl]-1H-pyrazole, 3-(β-D-glucopyranosyloxy)-4-[(4-isopropylphenyl)methyl]-5-methyl-1H-pyrazole, 3-(β-D-glucopyranosyloxy)-4-[(4-methylthiophenyl)methyl]-5-trifluoromethyl-1H-pyrazole, 3-(β-D-glucopyranosyloxy)-4-[(4-methoxyphenyl)methyl]-5-trifluoromethyl-1H-pyrazole, 3-(β-D-glucopyranosyloxy)-4-[(4-methoxyphenyl)methyl]-5-methyl-1H-pyrazole, 3-(β-D-glucopyranosyloxy)-1-methyl-4-[(4-methylthiophenyl)methyl]-5-trifluoromethylpyrazole, 3-(β-D-glucopyranosyloxy)-5-methyl-4-[(4-methylphenyl)methyl]-1H-pyrazole, 4-[(4-ethylphenyl)methyl]-3-(β-D-glucopyranosyloxy)-5-methyl-1H-pyrazole, 4-[(4-ethylphenyl)methyl]-3-(β-D-glucopyranosyloxy)-5-trifluoromethyl-1H-pyrazole, 3-(β-D-glucopyranosyloxy)-4-[(4-methoxyphenyl)methyl]-1,5-dimethylpyrazole, 3-(β-D-glucopyranosyloxy)-1-methyl-4-[(4-methylthiophenyl)-methyl]-5-trifluoromethylpyrazole, 1-ethyl-3-(β-D-glucopyranosyloxy)-4-[(4-methylthiophenyl)methyl]-5-trifluoro-methylpyrazole, 3-(β-D-glucopyranosyloxy)-4-[(4-methyl-thiophenyl)methyl]-1-propyl-5-trifluoromethylpyrazole, 3-(β-D-glucopyranosyloxy)-4-[(4-isopropoxyphenyl)methyl]-5-methyl-1-propylpyrazole, 1-ethyl-3-(β-D-glucopyranosyloxy)-4-[(4-isopropoxyphenyl)methyl]-5-methylpyrazole, 1-ethyl-3-(β-D-glucopyranosyloxy)-4-[(4-methoxyphenyl)-methyl]-5-methylpyrazole, 3-(β-D-glucopyranosyloxy)-4-[(4-methoxyphenyl)methyl]-5-methyl-1-propylpyrazole, 1-ethyl-4-[(4-ethoxyphenyl)methyl]-3-(β-D-glucopyranosyloxy)-5-methyl-1-propylpyrazole, 1-ethyl-4-[(4-ethylphenyl)-methyl]-3-(β-D-glucopyranosyloxy)-5-methylpyrazole, 4-[(4-ethylphenyl)methyl]-3-(β-D-glucopyranosyloxy)-5-methyl-1-propylpyrazole, 3-(β-D-glucopyranosyloxy)-4-[(4-isopropoxyphenyl)methyl]-1-isopropyl-5-methylpyrazole, 3-(β-D-glucopyranosyloxy)-5-methyl-4-{[4-(cyclopropylidenemethyl)-phenyl]methyl}-1H-pyrazole, 3-(β-D-glucopyranosyloxy)-5-methyl-4-(4-cyclopropylphenyl)methyl]-1H-pyrazole, (E)-4-{[4-(buta-1-en-1-yl)phenyl]methyl}-3-(β-D-glucopyranosyloxy)-5-methyl-1H-pyrazole, 3-(β-D-glucopyranosyloxy)-5-methyl-4-{[4-(thiazole-2-yl)phenyl]methyl}-1H-pyrazole, 3-(β-D-glucopyranosyloxy)-4-{[4-(3-hydroxypropyl)phenyl]-methyl}-5-trifluoromethyl-1H-pyrazole, 3-(β-D-glucopyranosyloxy)-5-methyl-4-{[4-(2-methylpropa-1-en-1-yl)-phenyl]methyl}-1H-pyrazole, 4-{[4-(4-fluorophenyl)phenyl]-methyl}-3-(β-D-glucopyranosyloxy)-5-methyl-1H-pyrazole, 4-{[4-(cyclobutyloxy)phenyl]methyl}-3-(β-D-glucopyranosyloxy)-5-methyl-1H-pyrazole, 3-(β-D-glucopyranosyloxy)-5-methyl-1-(cyclopropylmethyl)-4-[(4-cyclopropylphenyl)-methyl]-1H-pyrazole, 1-(cyclopropylmethyl)-3-(β-D-glucopyranosyloxy)-5-methyl-4-[(4-methylthiophenyl)methyl]-1H-pyrazole, 4-[(4-ethylphenyl)methyl]-3-(β-D-glucopyranosyloxy)-1-(3-hydroxypropyl)-5-methyl-1H-pyrazole, 2-(4-pyrazole-1-ylbenzyl) β-D-glucopyranoside, 2-[4-(4-hydroxypiperidin-1-yl)benzyl]phenyl β-D-glucopyranoside, 4-[(4-isopropoxyphenyl)methyl]-1-isopropyl-3-(6-O-methoxycarbonyl-β-D-glucopyranosyloxy)-5-methylpyrazole, 3-(6-O-ethoxycarbonyl-β-D-glucopyranosyloxy)-4-[(4-isopropoxyphenyl)-methyl]-1-isopropyl-5-methylpyrazole, 3-(6-O-isopropoxycarbonyl-β-D-glucopyranosyloxy)-4-[(4-isopropoxyphenyl)-methyl]-1-isopropyl-5-methylpyrazole, 3-(6-O-isobutoxycarbonyl-β-D-glucopyranosyloxy)-4-[(4-isopropoxyphenyl)-methyl]-1-isopropyl-5-methylpyrazole, 4-[(4-ethylphenyl)-methyl]-1-isopropyl-3-(6-O-methoxycarbonyl-β-D-glucopyranosyloxy)-5-methylpyrazole, 3-(6-O-ethoxycarbonyl-β-D-glucopyranosyloxy)-4-[(4-ethylphenyl)methyl]-1-isopropyl-5-methylpyrazole, 4-[(4-ethylphenyl)methyl]-3-(6-O-isopropoxycarbonyl-β-D-glucopyranosyloxy)-1-isopropyl-5-methylpyrazole, 4-[(4-ethylphenyl)methyl]-3-(6-O-isobutoxycarbonyl-β-D-glucopyranosyloxy)-1-isopropyl-5-methyl-pyrazole, 4-[(4-ethoxyphenyl)methyl]-1-isopropyl-3-(6-methoxycarbonyl-β-D-glucopyranosyloxy)-5-methylpyrazole, 3-(6-O-ethoxycarbonyl-β-D-glucopyranosyloxy)-4-[(4-ethoxyphenyl)methyl-1-isopropyl-5-methylpyrazole, 4-[(4-ethoxyphenyl)methyl]-3-(6-O-isopropoxycarbonyl-β-D-glucopyranosyloxy)-1-isopropyl-5-methylpyrazole, 3-(6-O-ethoxycarbonyl-β-D-glucopyranosyloxy)-1-isopropyl-4-[(4-methoxyphenyl)methyl]-5-methylpyrazole, 4-(4-ethoxyphenyl)-methyl]-3-(6-O-isobutoxycarbonyl-β-D-glucopyranosyloxy)-1-isopropyl-5-methylpyrazole, 1-isopropyl-3-(6-O-methoxycarbonyl-β-D-glucopyranosyloxy)-4-[(4-methoxyphenyl)-methyl]-5-methylpyrazole, 3-(6-O-isopropoxycarbonyl-β-D-glucopyranosyloxy)-1-isopropyl-4-[(4-methoxyphenyl)-methyl]-5-methylpyrazole, 3-(6-O-isobutoxycarbonyl-β-D-glucopyranosyloxy)-1-isopropyl-4-[(4-methoxyphenyl)-methyl]-5-methylpyrazole, 2-[(4-ethoxyphenyl)methyl]-4-(β-D-glucopyranosyl)-1-chlorobenzene, 1-isopropyl-3-(6-O-methoxycarbonyl-β-D-glucopyranosyloxy)-5-methyl-4-[(4-methylthiophenyl)methyl]pyrazole, 3-(6-O-ethoxycarbonyl-β-D-glucopyranosyloxy)-1-isopropyl-5-methyl-4-[(4-methylthiophenyl)methyl]pyrazole, 3-(6-O-isopropoxycarbonyl-β-D-glucopyranosyloxy)-1-isopropyl-5-methyl-4-[(4-methyl-thiophenyl)methyl]pyrazole, 3-(6-O-isobutoxycarbonyl-β-D-glucopyranosyloxy)-1-isopropyl-5-methyl-4-[(4-methyl-thiophenyl)methyl]pyrazole, 3-(4-ethylbenzyl)-2-(β-D-glucopyranosyloxy)-4,6-dimethylpyridine, 2-(β-D-glucopyranosyloxy)-3-(4-methoxybenzyl)-4,6-dimethylpyridine, 2-(β-D-glucopyranosyloxy)-3-{4-(2-hydroxyethyl)benzyl}-4,6-dimethylpyridine and 2-(β-D-glucopyranosyloxy)-6-methoxy-3-(4-methoxybenzyl)-4-methylpyridine For example, the above compounds can be prepared according to method described in the above Patent References 1 to 19 or an analogous method thereof.

In the present invention, the term "disease associated with abnormal accumulation of liver lipids" means a disease wherein the lipids including triglyceride accumulate abnormally in liver, a disease wherein the ratio of the amount of lipids to healthy cells of the liver and the liver weight increase abnormally, and the size of the liver increases abnormally. A progressive type wherein the accumulative amount of lipids further increases is also included. Moreover, a disease that shifts to other diseases because of the accumulation of lipids, and a disease with inflammation are also included. Concretely besides common fatty liver, non-alcoholic fatty liver disease (NAFL), non-alcoholic steatohepatitis (NASH), hypernutritive fatty liver, alcoholic fatty liver disease, toxic fatty livers diabetic fatty liver, acute fatty liver of pregnancy and the like can be illustrated.

The inhibitory effect on progression of the disease associated with abnormal accumulation of liver lipids can be confirmed by, for example, the examination that uses the KKA$^y$ mouse bearing the fatty liver. The present inventors confirmed that when 2-(4-methoxybenzyl)phenyl 6-O-ethoxycarbonyl-β-D-glucopyranoside of a SGLT2 inhibitor was orally administered to rat, the symptom that the lipid accumulative amount in rat liver increases is inhibited significantly in comparison with the case where the present compound is not administered. The above-mentioned result proves that a pharmaceutical composition comprising as an active ingredient a SGLT2 inhibitor is extremely useful as an agent for the inhibition of progression of a disease associated with abnormal accumulation of liver lipids.

In the present invention, it is possible to use the SGLT2 inhibitor of the active ingredient optionally in combination with one or more other drugs used for the fatty liver. For example, polyenphosphatidyl choline preparation, daisaikoto and the like can be illustrated as other drugs that can be used in combination. In addition, as far as the purpose of the present invention can be achieved, the SGLT2 inhibitor can be used in combination with a drug other than the above-mentioned drugs. In the case, metformin, troglitazone, pioglitazone hydrochloride, bezafibrate, voglibose and the like are illustrated as examples of the other drugs.

In the case of uses of the SGLT2 inhibitor in combination with the above one or more other drugs, either dosage form of simultaneous administration as a single preparation or separated preparations in way of the same or different administration route, and administration at different dosage intervals as separated preparations in way of the same or different administration route can be adopted.

The pharmaceutical compositions of the present invention can be prepared by suitably admixing with or by diluting and dissolving with an appropriate pharmaceutical additive pharmaceutically used depending on the compositions or the dosage form such as excipients, disintegrators, binders, lubricants, diluents, buffers, isotonicities, antiseptics, moistening agents, emulsifiers, dispersing agents, stabilizing agents, dissolving aids and the like, by formulating the mixture in accordance with conventional methods in dosage forms such as powders, granules, fine granules, dry syrups, tablets, capsules, solutions, injections, ointments, suppositories, poultices and the like, which can be orally or parenterally administered. The pharmaceutical compositions of the present invention also include a sustained release formulation including gastrointestinal mucoadhesive formulation (see, for example, International publications Nos. WO99/10010 and WO99/26606, and Japanese patent publication No. 2001-2567).

The dosage of a SGLT2 inhibitor in a pharmaceutical composition of the present invention is appropriately decided depending on the age, sex, body weight and degree of symptoms and treatment of each patient or the like, which is approximately within the range of from 0.1 to 1,000 mg per day per adult human in the case of oral administration and approximately within the range of from 0.01 to 300 mg per day per adult human in the case of parenteral administration. The daily dose can be divided into one to several doses per day and administered suitably. Also, in case of the uses of the drug(s) in combination with the other drug(s) other than SGLT2 inhibitors, the dosage of the SGLT2 inhibitor can be decreased depending on the dosage of the other drug(s) other than SGLT2 inhibitors.

Effect of the Invention

As mentioned above, the pharmaceutical compositions of the present invention which comprises as an active ingredient a SGLT2 inhibitor have an effect of the inhibition of progression of the disease associated with abnormal accumulation of liver lipids, and are highly suitable as an agent for the inhibition of progression of the disease associated with abnormal accumulation of liver lipids. Thence, the present invention can provide excellent pharmaceutical compositions that can inhibit the progression of the disease associated with abnormal accumulation of liver lipids by using a SGLT2 inhibitor without compelling patients the conventional dietary restriction by impossible diet therapy and the exercise therapy difficult to continue.

BEST MODE TO PRACTICE THE INVENTION

The present invention is further illustrated in more detail byway of the following Example. However, the present invention is not limited thereto.

EXAMPLE 1

Test to Confirm Inhibitory Effect on Accumulation of Liver Lipids

Using KKA$^y$ mice (KKAy/Ta Jcl, CLEA Japan, Inc.) as experimental animals, inhibitory effects on accumulation of lipids in liver based on SGLT2 inhibitory effects were evaluated. KKA$^y$ mice bearing fatty liver were prepared as follows.

Female 10-week-old KKA$^y$ mice were bred preparatorily for 4 weeks. During preparatory breeding until 4 days before grouping, the mice were fed on a pellet CE-2 diet for laboratory animal (CLEA Japan, Inc.) under free feeding. From 4 days before grouping, the food was changed to a powdered CE-2 diet for laboratory animal (CLEA Japan, Inc.). At the age of 14 weeks, body weight, blood glucose level and plasma alanine aminotransferase level (ALT) were measured for grouping. The mice were grouped (5 animals in each group) so that in any of these three laboratory values no significant difference was observed between the two groups. In the second group, the mice were fed on a powdered CE-2 diet for laboratory animal (CLEA Japan, Inc.) containing 1000 ppm of 2-(4-methoxybenzyl)phenyl 6-O-ethoxycarbonyl-β-D-glucopyranoside (hereinafter referred to as Compound A) as a SGLT2 inhibitor for 11 days, and then triglyceride contents in liver were measured. The results of the measurement were shown in Table 1. As a consequence, it was demonstrated that lipid accumulation in liver was significantly suppressed by administration of Compound A to KKA$^y$ mice bearing fatty liver, compared to drug-untreated mice. This indicates that SGLT2 inhibitors exhibit inhibitory effects on the progression of diseases associated with by abnormal lipid accumulation in liver.

Method of measurement of liver triglyceride content was described as follows.

1) Ice-cold saline (Otsuka Pharmaceutical Co., Ltd.) was added to liver in the proportion of 4 mL of ice-cold saline to 1 g of the liver, and then a homogenized suspension was prepared in a pestle homogenizer.
2) To 100 μL of the suspension 1), 800 μL of Folch reagent (chloroform:methanol=2:1) was added and mixed vigorously, and total lipids was extracted.
3) The mixture 2) was centrifuged (3000 rpm, for 10 min, at room temperature) using a cooled centrifuge (KUBOTA8900, KUBOTA Corporation).
4) The lower layer after centrifugation in 3) was collected and transferred to another container, and that is referred to as Solution (A).
5) To the upper layer after centrifugation in 3), 150 μL of Folch reagent was added and mixed vigorously, and centrifugation by the operation identical to that in 3) was performed. The lower layer was added to the Solution (A) described above.

6) To the Solution (A) obtained in 5), 250 µL of saline was added and mixed vigorously, and centrifugation by the operation identical to that in 3) was performed again.

7) The upper layer after centrifugation in 6) was removed by suction, and the solvent of the lower layer was removed under a nitrogen flow.

8) The residue 7) was dissolved by adding of 300 µL of Folch reagent.

9) From the solution 8), 10 µL of that was transferred to a RIAbeads tube (Dainabot Co., Ltd.), and the solvent was removed under a nitrogen flow.

10) Triglyceride was measured in a reaction in which 1.5 mL of a coloring reagent of Triglyceride E-test Wako (Wako Pure Chemical Industries, Ltd.) was added to the residue 9).

11) The liver triglyceride content per gram was calculated from the results obtained in 10). The data were expressed as the mean±standard error of the mean.

TABLE 1

| Group | Matter | Liver triglyceride content (mg/g liver) |
|---|---|---|
| The 1$^{st}$ group | Drug-untreated | 43.0 ± 5.7 |
| The 2$^{nd}$ group | Drug-treated (Compound A) | 25.4 ± 3.6* |

The symbol "*" in Table 1 means that there is a statistically significant difference (significance level is 5% or less) from the 1$^{st}$ group.

INDUSTRIAL APPLICABILITY

The pharmaceutical compositions of the present invention which comprises as an active ingredient a SGLT2 inhibitor have an effect of the inhibition of progression of the disease associated with abnormal accumulation of liver lipids, and are useful as an agent for the inhibition progression of a disease associated with abnormal accumulation of liver lipids.

The invention claimed is:

1. A method for the inhibition of progression of a disease associated with abnormal accumulation of liver lipids wherein the disease associated with abnormal accumulation of liver lipids is selected form the group consisting of non-alcoholic fatty liver disease (NAFL), non-alcoholic steatohepatitis (NASH), hypernutritive fatty liver, alcoholic fatty liver disease, diabetic fatty liver and acute fatty liver of pregnancy, which comprises administering to a subject an effective amount of 2-(4-methoxybenzyl)phenyl β-D-glucopyranoside or 2-(4-methoxybenzyl)phenyl 6-O-ethoxy-carbonyl-β-D-glucopyranoside, or a pharmaceutically acceptable salt thereof.

2. A method for the inhibition of progression of a disease associated with abnormal accumulation of liver lipids wherein the disease associated with abnormal accumulation of liver lipids is selected from the group consisting of non-alcoholic fatty liver disease (NAFL), non-alcoholic steatohepatitis (NASH), hypernutritive fatty liver, alcoholic fatty liver disease, diabetic fatty liver and acute fatty liver of pregnancy, which comprises administering to a subject an effective amount of 3(β-D-glucopyranosyloxy)-4-[(4-isopropoxyphenyl) methyl]-1-isopropyl-5-methylpyrazole or 3-(6-O-ethoxycarbonyl-(β-D-glucopyranosyloxy)-4-[(4-isopropoxyphenyl)-methyl]-1-isopropyl-5-methylpyrazole, or a pharmaceutically acceptable salt thereof.

3. A method for the inhibition of progression of a disease associated with abnormal accumulation of liver lipids wherein the disease associated with abnormal accumulation of liver lipids is selected from the group consisting of non-alcoholic fatty liver disease (NAFL), non-alcoholic steatohepatitis (NASH), hypernutritive fatter liver, alcoholic fatty liver disease, diabetic fatty liver and acute fatty liver of pregnancy as claimed in claim 1, which comprises administering to a subject an effective amount of 2-(4-methoxybenzyl)phenyl β-D-glucopyranoside or 2-(4-methoxybenzyl)-phenyl 6-O-ethoxycarbonyl-β-D-glucopyranoside, or a pharmaceutically acceptable salt thereof in combination with one or more selected from the group consisting of metformin, troglitazone, pioglitazone hydrochloride, bezafibrate and voglibose.

4. A method for the inhibition of progression of a disease associate with abnormal accumulation of liver lipids wherein the disease associated with abnormal accumulation of liver lipids is selected from the group consisting of non-alcoholic fatty liver disease (NAFL), non-alcoholic steatophepatitis (NASH), hypernutritive fatty liver disease (NAFL), non-alcoholic steatohepatitis (NASH), hypernutritive fatty liver, alcoholic fatty liver disease, diabetic fatty liver acute fatty liver of pregnancy as claimed in claim 2, which comprises administering to a subject an effective amount 3-(β-D-glucopyranosyloxy)-4-[(4-isopropoxyphenyl)methyl]-1-isopropyl-5-methylpyrazole or 3-(6-O-ethoxycarbonyl-β-D-glucopyranosyloxy)-4-[(4-isopropoxyphenyl)-methyl]-1-isopropyl-5-methylpyrazole, or a pharmaceutically acceptable salt thereof in combination with one or more materials selected from a group consisting of metformin, troglitazone, pioglitazone hydrochloride, bezafibrate and voglibose.

* * * * *